United States Patent
Andreasson et al.

(10) Patent No.: US 6,935,560 B2
(45) Date of Patent: Aug. 30, 2005

(54) SYSTEMS AND METHODS FOR TRACKING PHARMACEUTICALS WITHIN A FACILITY

(75) Inventors: Christer O. Andreasson, Escondido, CA (US); Jimmy C. Caputo, Carlsbad, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 168 days.

(21) Appl. No.: 10/085,472

(22) Filed: Feb. 26, 2002

(65) Prior Publication Data

US 2003/0164401 A1 Sep. 4, 2003

(51) Int. Cl.[7] ............................................. G06F 17/60
(52) U.S. Cl. ...................... 235/385; 235/381; 235/382; 340/5.92; 340/572.1; 700/236; 705/28
(58) Field of Search ................................ 235/385, 383, 235/381, 382, 382.5, 375; 340/568.1, 573.1, 572.1, 5.9, 5.92; 62/125; 700/231, 236, 237; 232/43.1; 705/28, 29

(56) References Cited

U.S. PATENT DOCUMENTS

| | | | |
|---|---|---|---|
| 4,164,320 A | 8/1979 | Irazoqui et al. | |
| 4,688,026 A | 8/1987 | Scribner et al. | |
| 4,717,042 A | 1/1988 | McLaughlin | |
| 4,785,969 A | 11/1988 | McLaughlin | |
| 4,839,806 A | 6/1989 | Goldfischer et al. | |
| 4,847,764 A | * 7/1989 | Halvorson | 700/231 |
| 4,853,521 A | 8/1989 | Claeys et al. | |
| 4,857,713 A | 8/1989 | Brown | |

(Continued)

FOREIGN PATENT DOCUMENTS

| | | |
|---|---|---|
| GB | 2309801 A | 8/1997 |
| WO | WO 96/05522 | 2/1996 |
| WO | WO 98/21124 | 5/1998 |
| WO | WO 99/10829 | 3/1999 |
| WO | WO 99/65548 | 12/1999 |
| WO | WO 00/04480 | 1/2000 |
| WO | WO 00/04521 | 1/2000 |
| WO | WO 00/62221 | 10/2000 |
| WO | WO 01/21131 A2 | 3/2001 |
| WO | WO 01/49343 | 7/2001 |
| WO | WO 01/97730 A2 | 12/2001 |
| WO | WO 02/21425 A2 | 3/2002 |
| WO | WO 02/43573 | 6/2002 |
| WO | WO 02/095675 A1 | 11/2002 |
| WO | WO 2003/048919 A1 * | 6/2003 |

*Primary Examiner*—Jared J. Fureman
(74) *Attorney, Agent, or Firm*—Orrick, Herrington & Sutcliffe, LLP (57) ABSTRACT

A medication-dispensing unit is provided for tracking medical products having a Radio Frequency Identification (RFID) tag uniquely associated therewith. The dispensing unit includes compartments for receiving medical products therein, and readers for reading the RFID tags associated with the medical products in the compartments. A processor is coupled to the readers for receiving and processing readings of the RFID tags in the compartment to identify the medical products in the compartments. The processor may identify a medical product removed from a compartment by determining a difference between readings of the RFID tags in the compartment taken before and after the medical product is removed from the compartment. The processor may verify that the medical product removed from the compartment is authorized to be removed or confirm that an identified patient is intended to receive the medical product being removed from the compartment.

28 Claims, 8 Drawing Sheets

U.S. PATENT DOCUMENTS

| | | |
|---|---|---|
| 4,857,716 A | 8/1989 | Gombrich et al. |
| 5,014,875 A | 5/1991 | McLaughlin et al. |
| 5,078,683 A | 1/1992 | Sancoff et al. |
| 5,104,374 A | 4/1992 | Bishko et al. |
| 5,207,642 A | 5/1993 | Orkin et al. |
| 5,317,506 A | 5/1994 | Coutrë et al. |
| 5,429,602 A | 7/1995 | Hauser |
| 5,460,294 A | 10/1995 | Williams |
| 5,520,450 A | 5/1996 | Colson, Jr. et al. |
| 5,624,400 A | 4/1997 | Firth et al. |
| 5,661,978 A | 9/1997 | Holmes et al. |
| 5,673,944 A | 10/1997 | Walker et al. |
| 5,716,114 A | 2/1998 | Holmes et al. |
| 5,732,401 A | 3/1998 | Conway |
| 5,739,508 A | 4/1998 | Uber, III |
| 5,805,456 A * | 9/1998 | Higham et al. .............. 700/236 |
| 5,818,021 A | 10/1998 | Szewczykowski |
| 5,842,976 A | 12/1998 | Williamson |
| 5,848,593 A | 12/1998 | McGrady et al. |
| 5,852,590 A | 12/1998 | de la Huerga |
| 5,865,470 A | 2/1999 | Thompson |
| 5,882,338 A | 3/1999 | Gray |
| 5,912,818 A | 6/1999 | McGrady et al. |
| 5,920,054 A | 7/1999 | Uber, III |
| 5,930,145 A * | 7/1999 | Yuyama et al. ............. 700/231 |
| 5,940,306 A | 8/1999 | Gardner et al. |
| 5,971,593 A | 10/1999 | McGrady |
| 5,973,600 A | 10/1999 | Mosher, Jr. |
| 5,991,729 A | 11/1999 | Barry et al. |
| 5,991,730 A | 11/1999 | Lubin et al. |
| 6,003,006 A | 12/1999 | Colella et al. |
| 6,021,392 A | 2/2000 | Lester et al. |
| 6,032,155 A | 2/2000 | de la Huerga |
| 6,039,249 A | 3/2000 | Szewczykowski |
| 6,055,506 A | 4/2000 | Frasca, Jr. |
| 6,055,507 A | 4/2000 | Cunningham |
| 6,065,819 A | 5/2000 | Holmes et al. |
| 6,073,834 A * | 6/2000 | Michael et al. ............. 232/43.1 |
| 6,104,295 A | 8/2000 | Gaisser et al. |
| 6,108,588 A | 8/2000 | McGrady |
| 6,108,634 A | 8/2000 | Podnar et al. |
| 6,109,774 A | 8/2000 | Holmes et al. |
| 6,110,152 A | 8/2000 | Kovelman |
| 6,112,182 A | 8/2000 | Akers et al. |
| 6,112,183 A | 8/2000 | Swanson et al. |
| 6,116,461 A | 9/2000 | Broadfield et al. |
| 6,123,686 A | 9/2000 | Olsen et al. |
| 6,148,297 A | 11/2000 | Swor et al. |
| 6,151,536 A * | 11/2000 | Arnold et al. .............. 700/237 |
| 6,154,726 A | 11/2000 | Rensimer et al. |
| 6,161,095 A | 12/2000 | Brown |
| 6,171,283 B1 | 1/2001 | Perez et al. |
| 6,219,587 B1 | 4/2001 | Ahlin et al. |
| 6,221,051 B1 | 4/2001 | Hjertman et al. |
| 6,256,967 B1 | 7/2001 | Hebron et al. |
| 6,259,654 B1 | 7/2001 | de la Huerga |
| 6,272,394 B1 * | 8/2001 | Lipps ........................ 700/231 |
| 6,294,999 B1 * | 9/2001 | Yarin et al. .............. 340/573.1 |
| 6,338,007 B1 * | 1/2002 | Broadfield et al. ......... 700/231 |
| 6,339,732 B1 | 1/2002 | Phoon et al. |
| 6,355,024 B1 | 3/2002 | Small et al. |
| 6,361,263 B1 | 3/2002 | Dewey et al. |
| 6,366,206 B1 | 4/2002 | Ishikawa et al. |
| 6,470,234 B1 * | 10/2002 | McGrady .................... 700/241 |
| 6,499,270 B2 | 12/2002 | Peroni et al. |
| 6,532,399 B2 * | 3/2003 | Mase ........................ 700/237 |
| 6,539,281 B2 * | 3/2003 | Wan et al. .................. 700/236 |
| 6,636,780 B1 * | 10/2003 | Haitin et al. ................ 700/236 |
| 6,658,322 B1 * | 12/2003 | Frederick et al. ........... 700/236 |
| 6,684,126 B2 * | 1/2004 | Omura et al. ............... 700/231 |
| 6,693,539 B2 * | 2/2004 | Bowers et al. ........... 340/572.1 |
| 2001/0028308 A1 | 10/2001 | De La Huerga |
| 2001/0032035 A1 * | 10/2001 | Holmes et al. ............. 700/231 |
| 2002/0023441 A1 | 2/2002 | Bara et al. |
| 2002/0026330 A1 | 2/2002 | Klein |
| 2002/0027507 A1 | 3/2002 | Yarin et al. |
| 2002/0038392 A1 | 3/2002 | De La Huerga |
| 2002/0067263 A1 | 6/2002 | Tafoya et al. |
| 2002/0067270 A1 | 6/2002 | Yarin et al. |
| 2002/0188259 A1 | 12/2002 | Hickle et al. |
| 2002/0195413 A1 | 12/2002 | Eastman et al. |
| 2004/0046020 A1 * | 3/2004 | Andreasson et al. ........ 235/385 |
| 2004/0054436 A1 * | 3/2004 | Haitin et al. ................ 700/236 |
| 2004/0094152 A1 * | 5/2004 | Harvey et al. ......... 128/203.15 |
| 2004/0108795 A1 * | 6/2004 | Meek et al. ................ 312/218 |

* cited by examiner

SYSTEMS AND METHODS FOR TRACKING PHARMACEUTICALS WITHIN A FACILITY

FIELD OF THE INVENTION

The present invention relates generally to systems and methods for dispensing medical products, and more particularly to systems and methods for tracking and/or monitoring removal of medical products from a medication-dispensing unit and/or for inventorying a medication-dispensing unit.

BACKGROUND OF THE INVENTION

In healthcare facilities, e.g., hospitals, medical products prescribed to patients may be temporarily stored in medication-dispensing units. Typically, a healthcare facility has one or more medication-dispensing units located on each floor and/or nursing station of the healthcare facility for storing medical products prescribed to patients on that floor. Each of the medication-dispensing units may include lockable storage compartments to limit access of the medical products contained therein to authorized healthcare workers. Controlled substances, such as morphine, may be segregated into individual storage compartments in a medication-dispensing unit to control access to these substances.

A healthcare worker, e.g., nurse, may log onto a medication-dispensing unit before administering medical products to patients. In order to authenticate the healthcare worker logging on, the dispensing unit may require the healthcare worker to scan an identification badge. Alternatively, the healthcare worker may gain access to the medical products in the dispensing unit with an electronic or manual key. Once logged on, the healthcare worker may pull up a list of patients assigned to him or her, including the medical products to be administered to the patients. The healthcare worker may then remove the medical products identified in the list of patients from the dispensing unit. In a further alternative, the dispensing unit may automatically grant the healthcare worker access to one or more individual storage compartments including medical products.

The inventory of medical products in a medication-dispensing unit may be monitored manually by requiring healthcare workers logged onto the dispensing unit to perform inventory checks of medical products in the dispensing unit, e.g., by counting the quantities of the medical products in the dispensing unit. The healthcare workers may then manually report their inventory checks to the dispensing unit, e.g., by entering inventory counts into the dispensing unit with a keypad or other input device. The healthcare workers may perform the manual inventory checks before and/or after removing medical products from the dispensing unit.

One problem with a manual approach for monitoring the inventory of medical products in a dispensing unit is that it relies on the accuracy of healthcare workers to manually check and report the inventory of medical products in the dispensing unit, which introduces human error. Another problem with a manual approach is that it may not prevent a dishonest healthcare worker from removing one or more unauthorized medical products, e.g., a controlled substance, from the dispensing unit. When this occurs, an unauthorized removal of a medical product may not be detected until another healthcare worker performs an inventory check of the medical product in the dispensing unit and detects a discrepancy. In this case, the healthcare worker detecting the discrepancy may report it to a healthcare administrator so that the administrator may investigate the discrepancy, e.g., by tracking down all of the healthcare workers that have logged onto the dispensing unit within a certain period of time. A problem with this approach is that a few days may pass before the unauthorized removal is detected, making it difficult to track down all of the healthcare workers. This may be especially troublesome if some of the healthcare workers are roaming nurses who only occasionally visit the healthcare facility in question.

Accordingly, automated systems and methods for tracking and/or monitoring removing medical products from a medication-dispensing unit would be considered useful.

SUMMARY OF THE INVENTION

The present invention is directed to systems and methods for monitoring or inventorying medical products within a healthcare facility, e.g., a hospital. This may include systems and methods for monitoring medical products entering and/or leaving a pharmacy, for dispensing medical products from a medication-dispensing unit, and/or for delivering medical products to individuals within the facility.

In accordance with one aspect of the present invention, an apparatus is provided for tracking medical products, each of the medical products having a Radio Frequency Identification (RFID) tag uniquely associated therewith. The apparatus includes a casing including one or more compartments for receiving one or more medical products therein. One or more readers are provided for reading the RFID tags associated with the medical products in the compartment. For example, a single reader may read the RFID tags of all of the medical products in the casing, or one or more readers may be provided for each compartment.

A processor is coupled to the reader for receiving and processing readings of the RFID tags in the compartment to identify the medical products in the compartment. The processor may identify a medical product removed from the compartment by determining a difference between readings of the RFID tags in the compartment taken before and after the medical product is removed from the compartment. Optionally, the processor may verify that the medical product removed from the compartment is authorized to be removed, e.g., by comparing a product identifier associated with the RFID tag of the removed medical product to a product identifier of a medical product authorized to be removed from the compartment. The product identifier may include at least one of a product name, a product serial number, a product lot number, and a patient identifier.

The apparatus may also include a display coupled to the processor for displaying a mismatch notification on the display when the processor detects a mismatch between the product identifier read from the RFID tag of the removed medical product and the product identifier of the medical product authorized to be removed. Optionally, the apparatus may include an input device coupled to the processor for identifying a patient to be associated with one or more medical products being removed from the compartment.

The apparatus may also include a return compartment for returning unused medical products, and a reader for reading an RFID tag of any returned medical product placed in the return compartment, the processor coupled to the reader for identifying the returned medical product.

In accordance with another aspect of the present invention, a method is provided for monitoring removal of medical products stored in a medication-dispensing unit, each of the medical products comprising a Radio Frequency Identification (RFID) tag uniquely associated therewith. The RFID tags of the medical products in an individual compartment or in the dispensing unit may be read before removing one or more medical products from the dispensing unit. One or more medical products may be removed from the dispensing unit, and then the RFID tags of the medical products remaining in the individual compartment or dispensing unit may be read after the one or more medical products are removed from the dispensing unit. A difference between the readings of the RFID tags taken before and after the one or more medical products are removed from the dispensing unit may be determined to identify the one or more medical products removed from the dispensing unit.

Optionally, the dispensing unit may automatically verify that the one or more medical products removed from the dispensing unit are authorized to be removed from the dispensing unit. For example, a product name identified by an RFID tag removed from the dispensing unit may be compared with a product name authorized to be removed from the dispensing unit. In addition or alternatively, a patient may be identified, and a product name identified by the RFID tag removed from the dispensing unit may be compared with a list of medical products scheduled for deliver to the identified patient.

In another option, the dispensing unit may transmit an inventory notice from the dispensing unit when a quantity of RFID tags stored within the dispensing unit falls below a threshold and/or to provide a current inventory of the contents of the dispensing unit.

In yet another option, a medical product may be returned to the dispensing unit, and the RFID tags of the medical products in the dispensing unit may be read before and after the medical product is returned to the dispensing unit. A difference between the readings of the RFID tags taken before and after the medical products are returned to the dispensing unit may be used to identify the medical product returned to the dispensing unit. In addition, an intended patient for the returned medical product may be identified, and a notice may be sent, e.g., to a pharmacy, doctor, administrator, and the like, that the intended patient did not receive the returned medical product.

It will be appreciated that any of these procedures, e.g., identifying medical products removed or returned to a dispensing unit, inventorying contents, and/or identifying intended patients, may be performed separately from one another or together.

In accordance with yet another aspect of the present invention, an apparatus is provided for monitoring administration of medical products to a patient, each of the medical products including a Radio Frequency Identification (RFID) tag for storing data related to the respective medical product. The apparatus includes a reader for substantially simultaneously reading RFID tags associated with a plurality of medical products to obtain the data stored in the RFID tags, and a processor coupled to the reader for comparing the data obtained from the RFID tags with data associated with a patient to verify that the patient is intended to receive the medical products. In a preferred embodiment, the reader is an antenna in a read pad for reading the RFID tags associated with the medical products when the medical products are placed in close proximity to the read pad, e.g., when the medical products are placed on a surface of the read pad.

Optionally, the apparatus may include an output device coupled to the processor; the processor activates the output device when the processor detects a mismatch between the data obtained from the RFID tags and the data associated with the patient.

During use, one or more medical products may be placed in close proximity to a RF antenna, e.g., the reader, and the Radio Frequency Identification (RFID) tags associated with the medical products may be read using the RF antenna to obtain the data stored in the RFID tags. Each of the plurality of medical products may be identified based upon the data obtained from the RFID tags. Optionally, data associated with a patient may be accessed, and the processor or a computer device communicating with the processor may verify that the patient is intended to receive the medical product by comparing the data obtained from the RFID tag with the data associated with the patient.

Other objects and features of the present invention will become apparent from consideration of the following description taken in conjunction with the accompanying drawings.

DESCRIPTION OF THE PREFERRED EMBODIMENTS

The present invention provides systems and methods for tracking and monitoring medical products within a healthcare facility, e.g., a hospital, clinic, or the like. The medical products may include vaccines, pharmaceuticals, or other therapeutic or diagnostic agents.

Figure 1A:
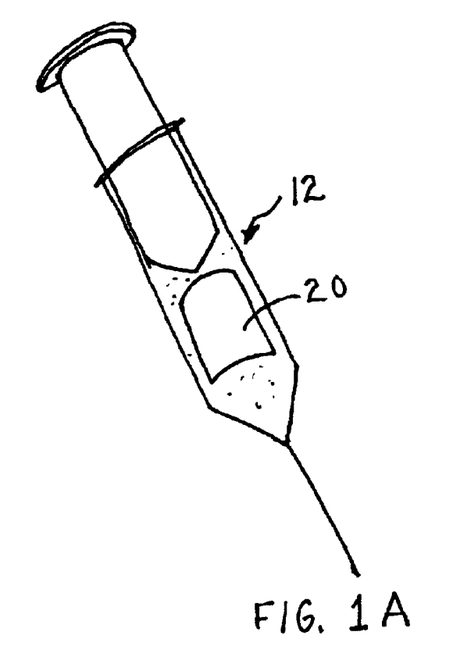
FIG. 1A shows a delivery device including an RFD tag, in accordance with the present invention.
Figure 1B:
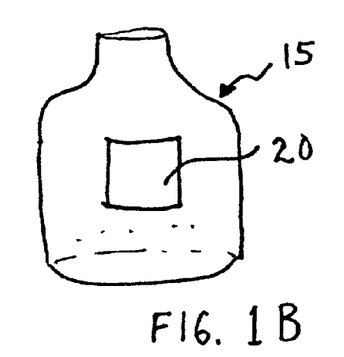
FIG. 1B shows a medical container including an RFID tag, in accordance with the present invention.

The medical products may be placed in drug delivery devices, such as syringes or other injection devices. FIG. 1A illustrates an exemplary drug delivery device 12 in the form of a syringe. Each of the drug delivery devices 12 may contain a unit dose of the medical product, such as a pre-filled syringe or ampoule. In addition, or alternatively, each of the delivery devices 12 may include a holder (not shown) within which a syringe or other medical cartridge may be received and/or a needle guard device (not shown) that may be attached to a syringe or medical cartridge. In a further alternative, the medical products may be placed in medical containers, such as bottles, vials, IV bags, pouches, and the like, or packaging (not shown) from which the medical products may be removed and administered to patients. FIG. 1B illustrates an exemplary medical container 15 in the form of a vial.

The medical products are tracked within the healthcare facility by attaching a radio frequency identification (RFID) tag 20 to each of the delivery devices 12 and/or medical containers 15 containing the medical products, as explained further below. FIGS. 1A and 1B show an exemplary RFID tag 20 attached to a delivery device 12 and a medical container 15, respectively. Each of the RFID tags 20 includes a write/read memory (not shown) for storing information and a built-in antenna (not shown) for communicating with a RF reader/writer. A RF reader may include an antenna for reading information stored in the RFID tag 20, e.g., by transmitting an RF interrogation signal to induce the RFID tag 20 to transmit its information to the RF reader, which is detected by the antenna. The RFID tag 20 may be active, i.e., powered by an internal power source, or passive, i.e., powered by a RF signal transmitted from the RF reader.

The RFID tag 20 attached to each of the delivery devices 12, medical containers 15, and/or packaging (not shown) stores information related to the medical product contained therein. The information in the RFID tag 20 may include product information, such as a serial number and/or a National Drug Code (NDC) associated with the medical product, a product name, a manufacture's name, a lot number, and/or an expiration date. Alternatively, the information in the RFID tag 20 may include a product identifier uniquely associated with one or more entries in a database that may be accessed to obtain information related to the medical product. The information in the RFID tag 20 may also include dosage information, identifying the amount and/or concentration of the medical product, and/or a patient identifier identifying a patient intended to receive the medical product. Other optional information may include administration requirements, instructions for use and/or product warning, such as possible allergic reactions or adverse interaction of the product with other medical products. Other information that may be stored in the RFID tag 20 is given below. Information may be written into the RFID tag 20 by the manufacturer of the medical product and/or the healthcare facility receiving the medical product. Some or all of the information in the RFID tag 20 may also be printed on the outer surface of the RFID tag 20 so that a healthcare worker may visually read the information.

Each of the RFID tags 20 may be made thin and flexible, allowing the RFID tag 20 to be attached to a delivery device 12, medical container 15, and/or packaging (not shown) so that it does not interfere with using the delivery device 12 or medical container 15. For example, an RFID tag 20 may be affixed around the barrel of a syringe 12, as illustrated in FIG. 1A.

RFID tags 20 offer several advantages over conventional barcode tags. For example, a RF reader does not require a line of sight between itself and a RFID tag 20 to read the information in the RFID tag 20. In addition, a RF reader may read many RFID tags 20 at a time, while a barcode reader or scanner can only read one barcode tag at a time. Furthermore, RFID tags 20 may be smaller, more accurate, more durable, and may be capable of storing more information than barcode tags.

Figure 2:
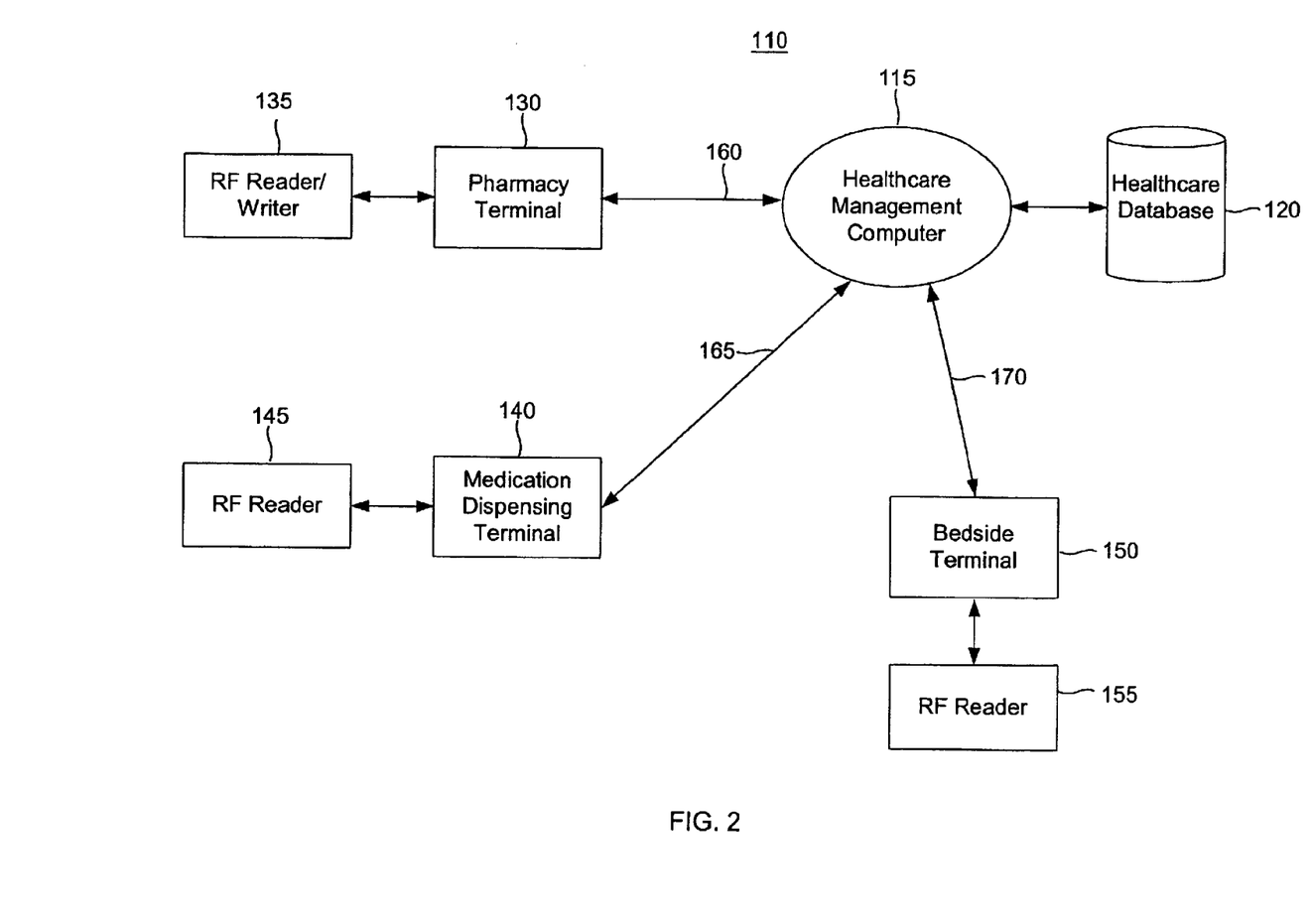
FIG. 2 shows an embodiment of a system for tracking and monitoring medical products, in accordance with the present invention.

FIG. 2 is a diagram illustrating a system 110 for tracking and monitoring medical products according to an exemplary embodiment of the invention. The system 110 may be implemented at a healthcare facility, such as a hospital, a nursing home, a clinic, or the like.

The system 110 includes a healthcare management computer 115 and a healthcare database 120. The healthcare management computer 115 manages and stores information related to the operation of the healthcare facility in the healthcare database 120. The management computer 115 may be a central computer and/or a network of computers and may or may not be physically located on the premises of the healthcare facility. The system 110 also includes a pharmacy terminal 130 coupled to a RF reader/writer 135 and a medication dispensing terminal 140 coupled to a RF reader 145. The system 110 further includes a bedside terminal 150 coupled to a RF reader 155, which may be located at or near the bedside of a patient (not shown). Each of the terminals 130,140,150 preferably includes a processor, memory, an input device, and an output device (all not shown) for performing the tasks described below. In addition, each of the RF readers 135,145,155 may be built into their respective terminal 130,140,150. Each of the terminals 130,140,150 may be linked to the management computer 115 via communications links 160,165,170, respectively. The communications links 160,165,170 may be cable links, optical links, and/or wireless links, e.g., short-range RF links. Preferably, each of the terminals 130,140, 150 may access patient and/or medical product information stored in the healthcare database 120 via the communications links 160,165,170.

The information stored in the healthcare database 120 may include a patient file uniquely associated with each individual patient admitted in the healthcare facility. Each of the patient files may include the patient's name, address, social security number, and/or patient ID, which may be assigned to the patient upon admission to the healthcare facility. Each of the patient files may also include the medical products prescribed to the respective patient and/or a record of the medical products administered to the respective patient, including dates and time of administration, the healthcare worker who administered the medical products, and the like. Each of the patient files may also include the current location of the respective patient within the healthcare facility, e.g., the floor and/or room number of the patient in the healthcare facility. The information in the database 120 may further include insurance billing information for each individual patient, including the name, telephone number, billing address, and/or group ID of the patient's insurer. In addition, the information in the database 120 may include a healthcare worker file associated with each individual healthcare worker working at the healthcare facility. Each of the healthcare worker files may include reports reflecting the work performance of the healthcare worker, as explained further below. Additional information that may be stored in the database 120 is given below.

Figure 3:
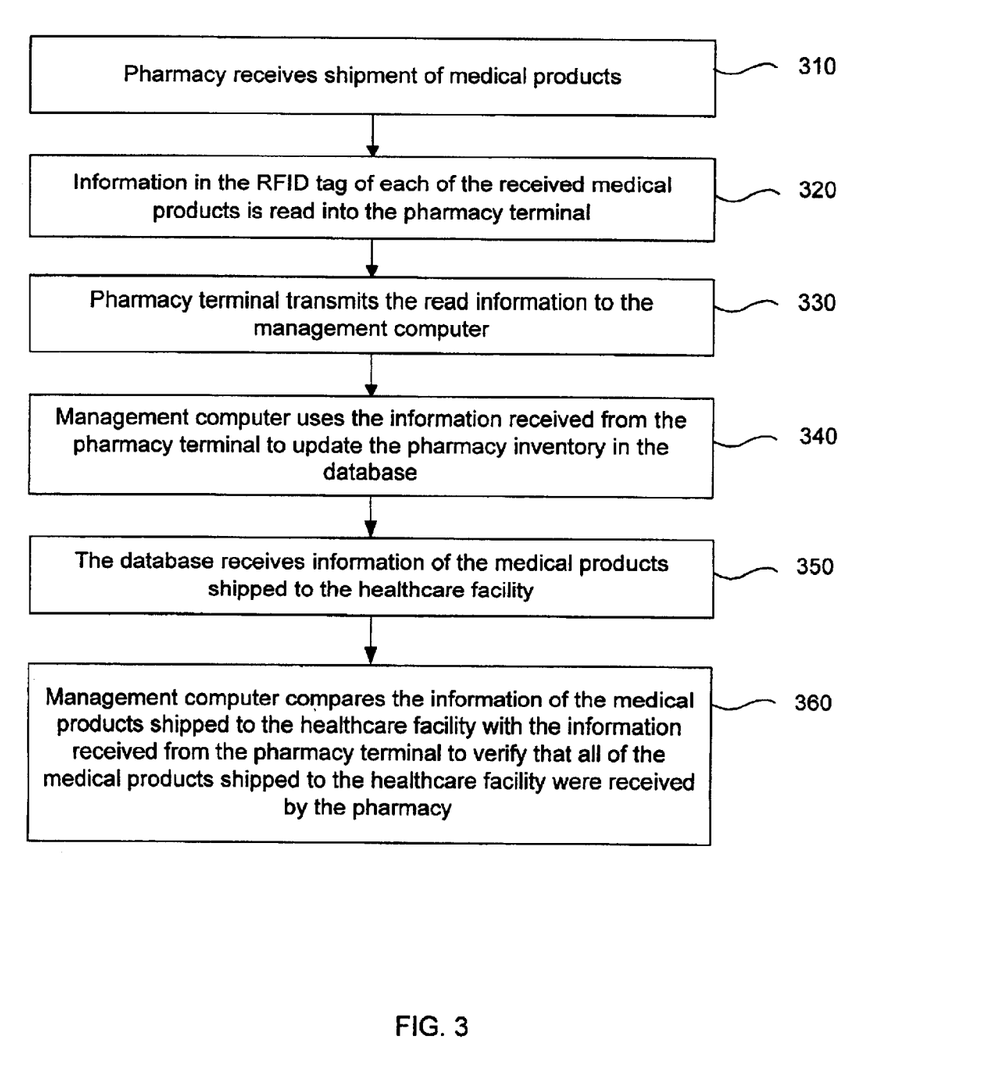
FIG. 3 is a flowchart, showing a method for tracking the inventory of medical products in a pharmacy, in accordance with the present invention.

Turning to FIG. 3, a method for tracking the inventory of medical products in a pharmacy of the healthcare facility will now be described according to an embodiment of the invention. The healthcare database 120 in this embodiment includes a pharmacy inventory of the medical products stored in the pharmacy.

In step 310, the pharmacy receives a shipment of medical products. Preferably, each of the medical products may be identified by an RFID tag 20, which may be attached to a delivery device 12 and/or medical container 15 containing the medical product. Each of the RFID tags 20 may include product information for the associated medical product, including a serial number and/or a NDC, the product name, the manufacturer's name, a lot number, and/or an expiration date. Alternatively, or in addition, each of the RFID tags 20 may include a product identifier uniquely associated with one or more entries in a database that may be accessed to obtain information related to the associated medical product.

In step 320, the product information in the RFID tags 20 of the received medical products is read into the pharmacy terminal 130 using the RF reader 135. In step 330, the pharmacy terminal 130 transmits the product information read from the RFID tags 20 of the received medical products to the management computer 115 via the communications link 160. In step 340, the management computer 115 uses the received information to update the pharmacy inventory in the database 120 accordingly. The pharmacy inventory may be updated to include the product name, amount, and/or expiration date of each of the medical products received by the pharmacy.

In an optional step 350, the database 120 receives information of the medical products shipped to the healthcare facility from the manufacturer. This information may be downloaded into the database 120 from a remote manufacturer database (not shown) via, e.g., an Internet link, from a CD-ROM disc included with the medical product shipment, or the like. The information of the medical products shipped to the healthcare facility may include the serial number, NDC, and product name of each of the medical products shipped to the healthcare facility.

In step 360, the management computer 115 compares the information of the medical products shipped to the healthcare facility with the information received from the pharmacy terminal 130 to verify that all of the medical products shipped to the healthcare facility were received by the pharmacy. This comparison may be carried out, e.g., by having the management computer 115 compare the serial numbers of the medical products shipped to the healthcare facility with the serial numbers read from the RFID tags 20 of the received medical products. If the management computer 115 detects a mismatch between the medical products shipped to the healthcare facility and the medical products received by the pharmacy in step 360, the management computer 115 may transmit a notification of the detected mismatch to the pharmacy terminal 130. The notification may then be displayed to a healthcare worker at the pharmacy, e.g., via a display (not shown) at the pharmacy terminal 130. The notification may include specific information of the mismatch, such as the identity of any shipped medical products missing from the pharmacy.

In one embodiment, the management computer 115 automatically orders a medical product from a manufacturer and/or wholesaler when the amount of the medical product stored in the pharmacy 130 drops below a predetermined minimal level. This may be done, e.g., by having the management computer 115 monitor the amount of the medical product in the pharmacy using the pharmacy inventory in the database 120. When the amount of the medical product in the pharmacy inventory drops below the minimal level, the management computer 115 may place an electronic order for the medical product to a manufacturer computer, e.g., via an Internet link.

When a physician prescribes a medical product to a patient, the prescription is forwarded to the pharmacy, e.g., electronically or in the form of a handwritten prescription. The prescription may include the frequency, dosage, and duration that the medical product is to be administered to the patient. The prescription may also be sent to the management computer 115 to be included in the associated patient file in the healthcare database 120. A pharmacist at the pharmacy may prepare the prescribed medical product for administration to the patient in accordance with the prescription. This may involve transferring and/or admixing unit doses of the prescribed medical product from a bulk medical container into separate delivery devices 12. Preferably, each of the delivery devices 12 has a RFID tag 20 attached thereon into which information related to the medical product contained therein may be written using the RF writer 135. The written information may include the product name and dosage of the medical product in the delivery device, and/or the name, patient ID and/or the location of the patient intended to receive the medical product. In addition, the written information may include the identity of the pharmacist or other health care worker preparing the medical product and/or the date and time that the medical product was prepared.

Alternatively, or in addition, the prescribed medical product may be shipped to the pharmacy from the manufacturer in unit-dose delivery devices 12 or medication containers 15, e.g., vials, bottles, bags, and the like. In this case, the pharmacist may use the RF writer 135 to write additional information into each of the RFID tags 20 attached to the delivery devices 12 and/or medication containers 15, including the name, patient ID and/or location of the patient intended to receive the medical product. Optionally, individual delivery devices 12 and/or medication containers 15 may be assigned to individual patients as they are removed from a dispensing unit (not shown), as described further below.

After the medical product is prepared for the patient, the medical product may be grouped with other prepared medical products for transport to a medication-dispensing unit. As the medical products are withdrawn from the pharmacy for transportation to the medication-dispensing unit, the information in the RFID tags 20 of the medical products may be read into the pharmacy terminal 130 using the RF reader 135. For example, all of the medical products may be identified by passing a cart or other device carrying the medical products into close proximity with the RF reader 135, thereby simultaneously reading all of the RFID tags 20 identifying the medical products. For example, the RF reader 135 may be mounted to a doorway of the pharmacy for automatically reading the RFID tags 20 of the medical products as they are withdrawn from the pharmacy. The pharmacy terminal 130 may also identify the medication-dispensing unit intended to receive the medical products. This may be done by having a healthcare worker manually enter the identity of the dispensing unit into the pharmacy terminal 130, and/or reading a RFID tag identifying the dispensing unit using the RF reader 135. This may also be done by reading a patient identifier and/or location from the RFID tags 20 of the medical products into the pharmacy terminal 130 and having the pharmacy terminal 130 access a database matching the patient identifier and/or location with an assigned dispensing unit. The pharmacy terminal 130 may also identify the healthcare worker transporting the medical products to the dispensing unit. This may be done by having the healthcare worker enter a code and/or pin number uniquely associated with the healthcare worker into the pharmacy terminal 130, and/or reading a RFID tag identifying the healthcare worker using the RF reader 135.

The pharmacy terminal 130 may then transmit the information read from RFID tags 20 of the medical products to the management computer 115 via the communications link 160. The pharmacy terminal 130 may also transmit the identity of the dispensing unit to receive the medical products and/or the identity of the healthcare worker transporting the medical products to the dispensing unit. The management computer 115 uses the received information to record the medical products being withdrawn from the pharmacy in the database 120 and to update the pharmacy inventory in the database 120 accordingly. The record of the medical products being withdrawn from the pharmacy may include the product name and amount of each of the medical product being withdrawn. The record may also include the date and time that the medical products are withdrawn from the pharmacy, the identity of the dispensing unit to receive the medical products, and/or the identity of the healthcare worker transporting the medical products to the dispensing unit.

Medication-dispensing units may be placed throughout the medical facility for temporarily storing medical products and for dispensing the medical products to healthcare workers, e.g., nurses, assigned to administer the medical products to patients. Each of the medication-dispensing units, e.g., stationary medication stations and/or movable medication carts, may be located on the same floor, wing, and the like of the healthcare facility as the patients intended to receive the medical products stored therein.

Figure 4:
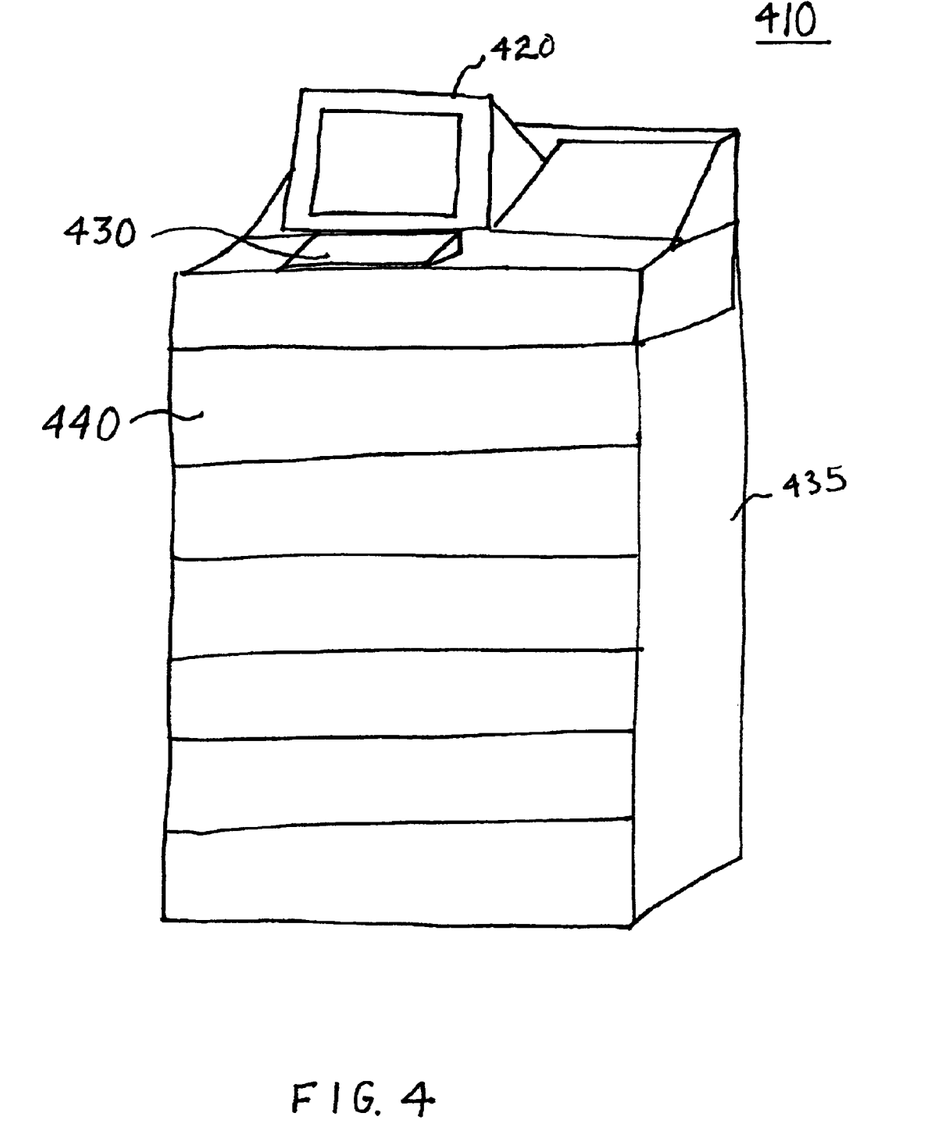
FIG. 4 shows an embodiment of a medication-dispensing unit, in accordance with the present invention.

FIG. 4 illustrates an exemplary medication-dispensing unit 410 according to an embodiment of the invention. The dispensing unit 410 includes a casing 435 including one or more and preferably a plurality of storage compartments 440 for storing medical products therein. Each of the storage compartments 440 may store medical products for an individual patient or for general use. The dispensing unit 410 may include lockable doors for controlling access to the storage compartments 440. Alternatively, or in addition, the dispensing unit 410 may include lockable drawers that may be pulled out from the storage compartments 440.

The dispensing unit further includes a medication-dispensing terminal 140 and a RF reader 145 (not shown in FIG. 4). The dispensing terminal 140 further includes a display 420, e.g., a monitor, and an input device 430, e.g., a touch screen or keypad, as illustrated in FIG. 4.

Preferably, the RF reader 145 is configured to read the RFID tags 20 inside the storage compartments 440 of the dispensing unit 410. To accomplish this, the RF reader 145 may be made up of a plurality of RF readers, each of the RF readers configured to read the RFID tags 20 in one of the storage compartments 440. Alternatively, a single RF reader may be used to read the RFID tags 20 of the entire contents of the dispensing unit 410.

Optionally, the dispensing unit 410 may include one or more return compartments or bins (not shown) for unused medical products, as explained further below. Each return bin may include a slot or drawer (not shown) for placing one or more medical products therein, e.g., such that the medical products cannot be removed from the return bin without gaining authorization to override a lock and open the return bin. Each return bin may include a RF reader for reading the RFID tags of any returned medical products placed in the return bin, e.g., to inventory returned medical products. Alternatively, a single RF reader of the dispensing unit 410 may read any RFID tags of medical products in the return bin, along with the RFID tags of medical products in the other compartments.

Figure 5:
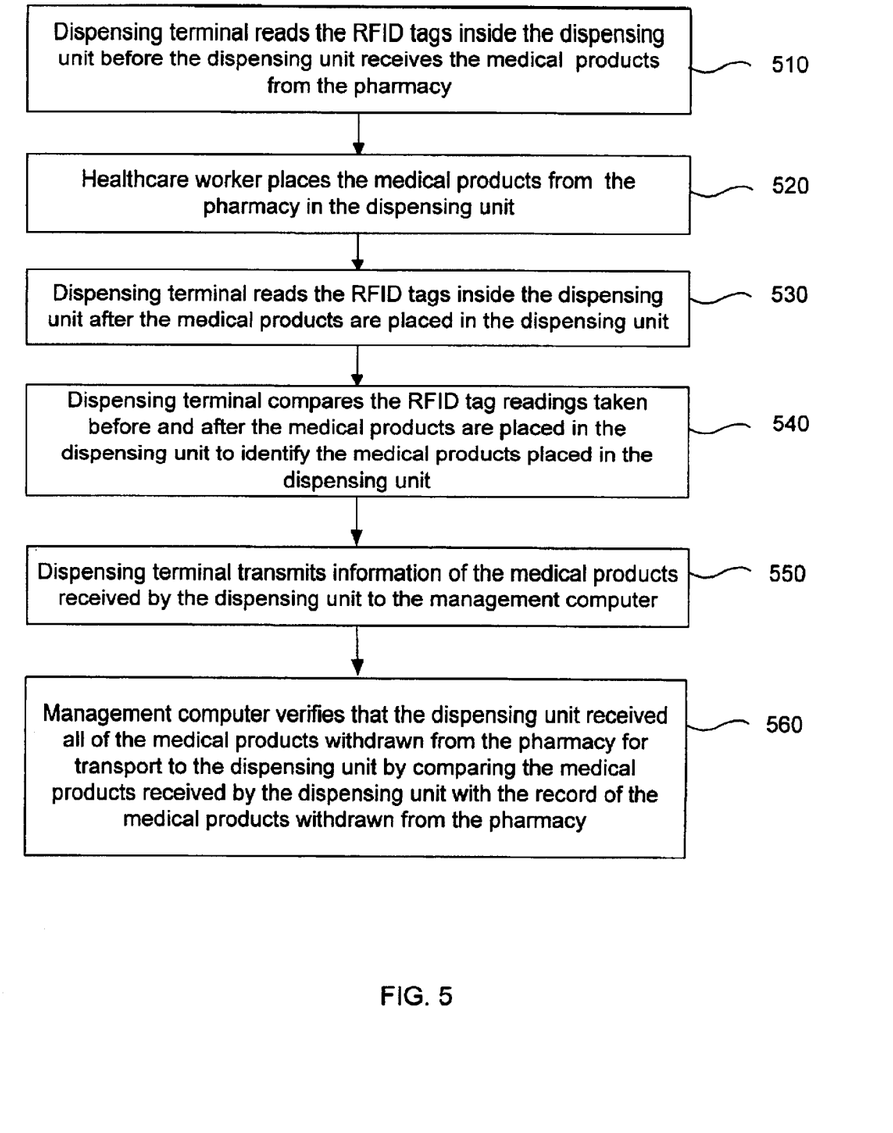
FIG. 5 is a flowchart, showing a method for verifying that a medication-dispensing unit receives medical products, in accordance with the present invention.

Turning to FIG. 5, a method for verifying that the medical products transported to the dispensing unit 410 from the pharmacy are received by the dispensing unit 410 is described according to a preferred embodiment. In this embodiment, the healthcare database 120 includes a dispensing unit inventory of the medical products in the dispensing unit 410.

In step 510, the dispensing terminal 140 reads the RFID tags 20 inside the dispensing unit 410 before the dispensing unit 410 receives the medical products from the pharmacy. In step 520, a healthcare worker places the medical products from the pharmacy in the dispensing unit 410. In step 530, the dispensing terminal 140 reads the RFID tags 20 inside the dispensing unit 410 after the medical products are placed in the dispensing unit 410. In step 540, the dispensing terminal 140 identifies the medical products placed in the dispensing unit 410 by determining the difference between the RFID tag readings taken before and after the medical products are placed in the dispensing unit 410. Alternatively, the dispensing terminal 140 may transmit the RFID tag readings to the management computer 115 so that the management computer 115 may identify the medical products placed in the dispensing unit. In step 550, the dispensing terminal 140 transmits information of the medical products received by the dispensing unit 410 to the management computer 115 via the communications link 165. This information may include the product information read from the RFID tags 20 of the received medical products. The management computer 115 uses the information received from the dispensing terminal 130 to update the dispensing unit inventory in the database 120 accordingly.

In step 560, the management computer 115 may verify that the dispensing unit 410 received all of the medical products withdrawn from the pharmacy for transport to the dispensing unit 410 by, e.g., comparing the medical products received by the dispensing unit 410 with the record of the medical products withdrawn from the pharmacy. If the management computer 115 detects a mismatch between the medical products received by the dispensing unit 410 and the medical products withdrawn from the pharmacy, the management computer 115 may transmit a notification of the detected mismatch to the dispensing terminal 140 via communications link 165. The dispensing terminal 140 may then notify the healthcare worker at the dispensing unit 410 of the mismatch, e.g., via the display. The notification may include specific information of the mismatch, such as the identity of any medical products missing from the dispensing unit 410. The dispensing terminal 140 may then give the healthcare worker an opportunity to correct the mismatch, e.g., by repeating the above steps 520 through 560. The management computer 115 may include a report of the mismatch in the associated healthcare worker file, including whether the healthcare worker corrected the mismatch and/or specific information of the mismatch, such as the identity of missing medical products. If the healthcare worker fails to correct the mismatch, the management computer 115 may notify a healthcare administrator via a terminal display (not shown) linked to the management computer 115 so that the healthcare administrator may take appropriate action.

In one embodiment, the management computer 115 periodically performs an inventory check of the medical products in the dispensing unit 410 to detect any unauthorized removal of medical products from the dispensing unit 410. The management computer 115 may check the inventory of the dispensing unit 410 by transmitting a request to the dispensing terminal 130, via the communications link 160, to read the RFID tags 20 of the medical products inside the dispensing unit 410. After reading the RFID tags 20, the dispensing terminal 130 may transmit information from the read RFID tags 20 to the management computer 115. The management computer 115 may then compare the information from the read RFID tags 20 with the dispensing unit inventory stored in the database 120. If the management computer 115 detects a mismatch, then the management computer 115 may notify a healthcare administrator of the mismatch via a terminal display (not shown) linked to the management computer 115. The notification may include the identity of any medical products missing from the dispensing unit 410. In a further embodiment, a healthcare worker at a terminal (not shown) linked to the management computer 115 may remotely request the management computer 115 to perform an inventory check of the dispensing unit 410, e.g., to seek a dispensing unit for a needed or missing medical product.

Figure 6:
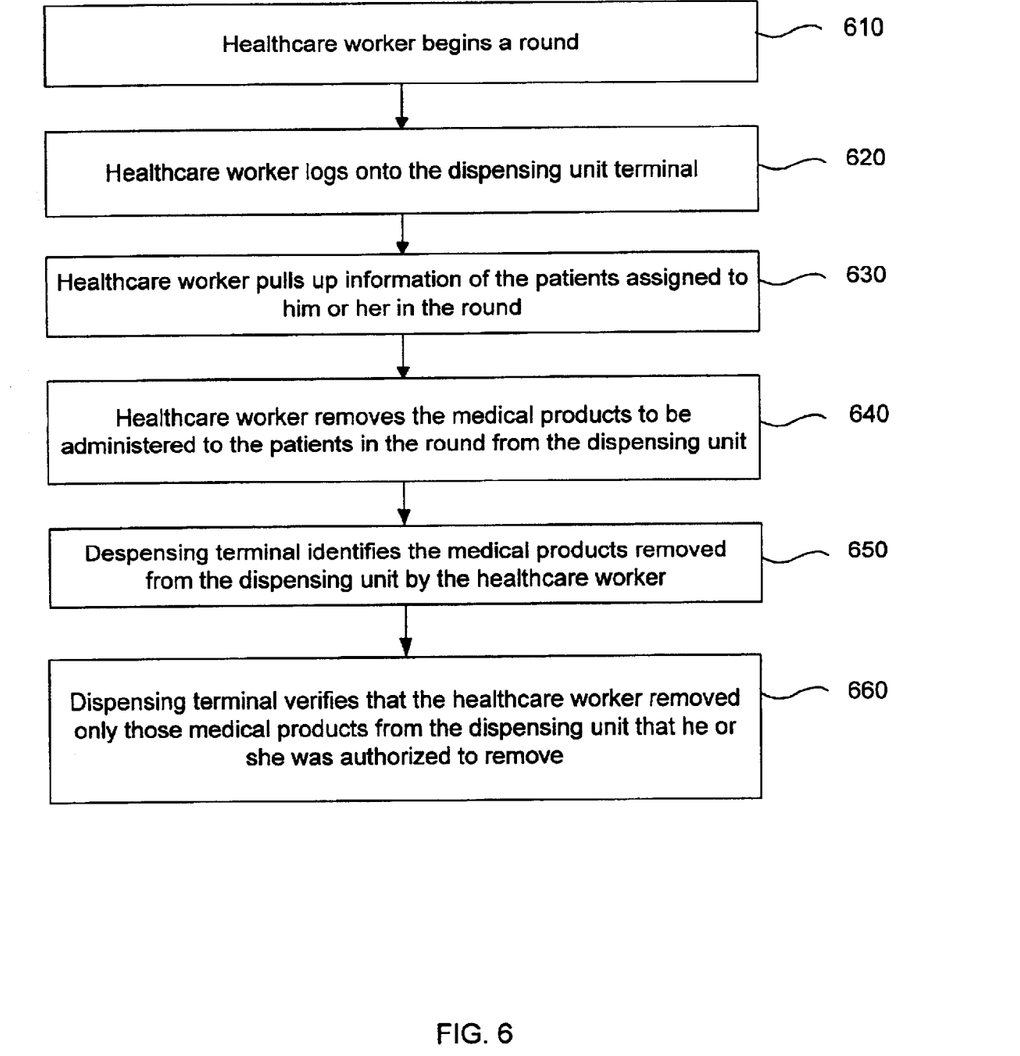
FIG. 6 is a flowchart, showing a method for verifying that a healthcare worker only removes medical products from the dispensing unit that he or she is authorized to remove, in accordance with the present invention.

Turning to FIG. 6, a method for verifying that a healthcare worker, e.g., nurse, only removes those medical products from the dispensing unit 410 for the patients assigned to him or her will now be described.

In step 610, the healthcare worker may begin or resume a round, in which he or she is to administer medical products to patients assigned to him or her in the round. In step 620, the healthcare worker may log onto the dispensing terminal 140, e.g. by swiping an electronic card, by entering a PIN number uniquely associate with the healthcare worker into the input device, or by reading an RFID tag worn by the healthcare worker. In step 630, once the healthcare worker is logged on, he or she may pull up information of the patients assigned to him or her in the round, which is displayed on the display. The information may include the patients' names and the medical products to be administered to the patients in the round. The information may be preloaded in the dispensing terminal 140 or downloaded into the dispensing terminal 140 from the associated patient files in the database 120 via the communications link 165.

In step 640, the healthcare worker removes the medical products to be administered to the patients in the round from the dispensing unit 410. The healthcare worker may gain access to the medical products by having the dispensing unit 410 automatically open the doors to the storage compartments 440 containing the medical products to be removed. Alternatively, the healthcare worker may use an electronic or manually key to gain access to the storage compartments 440 containing the medical products to be removed. In step 650, the dispensing terminal 140 identifies the medical products removed from the dispensing unit 410 by the healthcare worker. The dispensing terminal 140 may do this, e.g., by reading the RFID tags 20 inside the dispensing unit before and after the healthcare worker removes the medical products from the dispensing unit 410. The dispensing terminal 140 may then determine the difference between the two RFID tag readings to detect removal of the RFID tags 20, and consequently the medical products having the RFID tags 20, from the dispensing unit 410, and thereby identify the medical products removed from the dispensing unit 410.

In step 660, the dispensing terminal 140 may verify that the healthcare worker removed only those medical products that he or she was authorized to remove. The dispensing terminal 140 may do this, e.g., by comparing the medical products removed from the dispensing unit 410 with the medical products to be administered in the round. For example, the dispensing terminal 140 may compare the product names and/or dosages of the removed medical products with the product names and/or dosages of the medical products to be administered in the round. The dispensing terminal 140 may obtain the names and/or dosages of the removed medical products from the RFID tag reading taken before the medical products are removed from the dispensing unit 410. The product names and dosages of the medical products to be administered in the round may be downloaded from the associated patient files in the database 120. Alternatively, or in addition, the dispensing terminal 140 may compare the intended patients of the removed medical products with the patients to be administered in the round.

If the dispensing terminal 140 detects a mismatch between the medical products removed from the dispensing unit and the medical products to be administered during the round, the dispensing terminal 140 may notify the healthcare worker of the detected mismatch via the display 420. Alternatively, or in addition, the dispensing terminal 140 may notify the healthcare worker using an audio indicator, e.g., buzzer, and/or a visual signal indicator, e.g., a flashing light. The dispensing terminal 140 may provide the healthcare worker, via the display 420, with the specifics of the detected mismatch, such as the identity of medical products that the healthcare worker was not authorized to remove from the dispensing unit 410. The dispensing terminal 140 may then give the healthcare worker an opportunity to correct the mismatch, e.g., by returning an unauthorized medical product to the dispensing unit 410 and repeating steps 640–650. The unauthorized medical product(s) may be returned to the compartment(s) from which it(they) were removed, or may be placed in a return bin, specifically intended for returned medical products.

The dispensing terminal 140 may transmit information of the medical products removed from the dispensing unit 410 to the management computer 115 via the communications link 160. The information may include the product information and intended patients of the removed medical products. The management computer 115 may use the received information from the dispensing terminal 140 to update the dispensing unit inventory in the database 120 accordingly. The received information may also include any detected mismatch that occurred during removal of the medical products from the dispensing unit 410. If a mismatch occurs, the management computer 115 may include a report of the mismatch in the associated healthcare worker file, including specific information of the mismatch and whether the healthcare worker corrected the mismatch. Such a report may allow the healthcare facility administration to evaluate the work performance and/or honesty of the healthcare worker.

After retrieving the medical products from the dispensing unit 410, the healthcare worker may visit the patients assigned to him or her in the round to administer the medical products. While visiting each patient in the round, the healthcare worker may administer the medical products prescribed to that patient.

Figure 7:
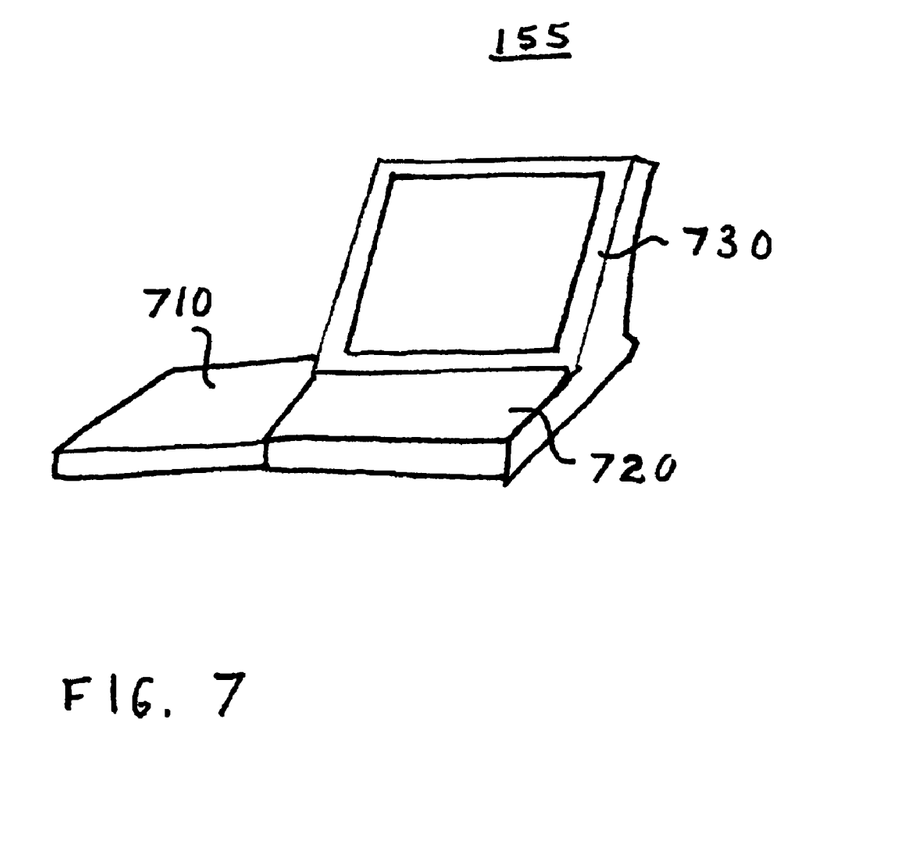
FIG. 7 shows an embodiment of a bedside terminal, in accordance with the present invention.

Each of the patients may be provided with a bedside terminal 150 for verifying that the patient receives the correct medical products during the round. FIG. 7 illustrates an exemplary bedside terminal 150 according to an embodiment of the invention. The bedside terminal 150 may include a RF read pad 710 having a built-in RF reader 155 (not shown in FIG. 7), an input device 720, e.g., a keypad or a touch screen, and an output device 730, e.g., an LCD display, or a sound or visual indicator. The RF reader 150 may be configured to read the RFID tags 20 of medical products placed onto the RF read pad 710. Alternatively, the RF reader 155 may be a separate device coupled to the bedside terminal 150, e.g., via a direct or wireless link. For example, the RF reader 155 may be a separate device located at an entrance, e.g., doorway, of a patient's room for automatically reading the RFID tags 20 of medical products as a healthcare worker carrying the medical products enters the patient's room.

Figure 8:
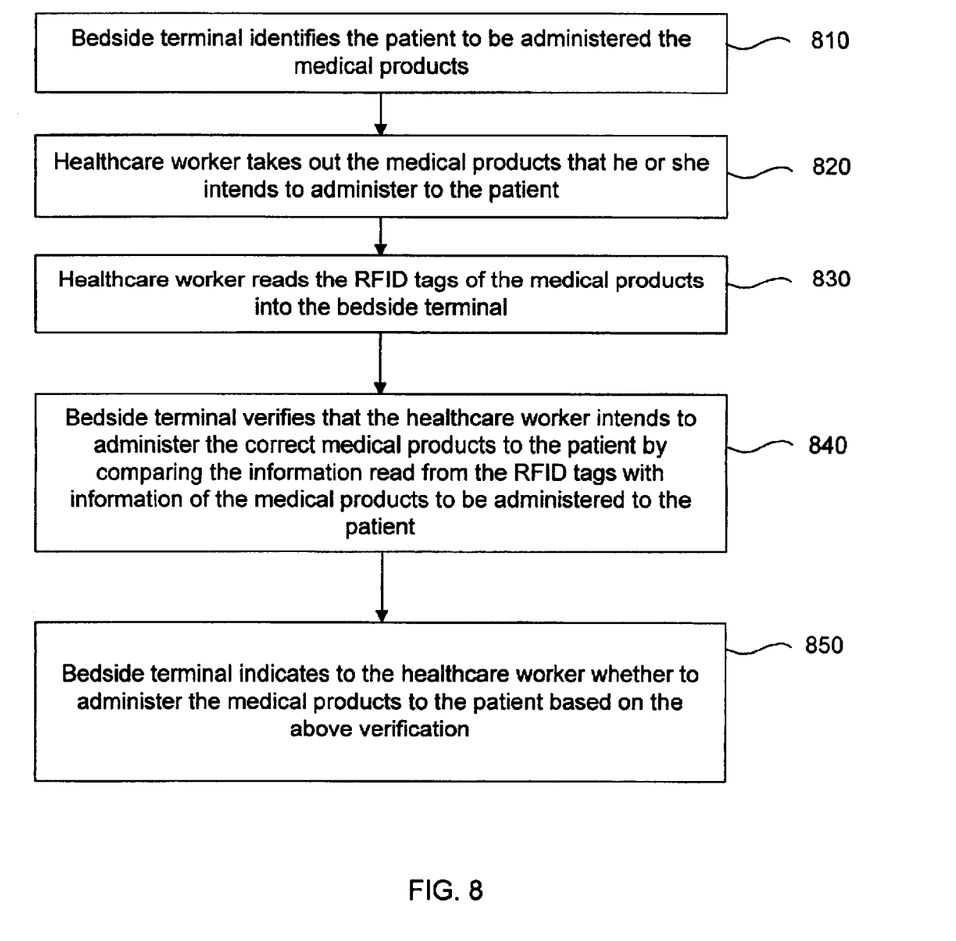
FIG. 8 is a flowchart, showing a method for verifying that a healthcare worker intends to administer the correct medical products to a patient, in accordance with the present invention.

Turning now to FIG. 8, a method for verifying that the healthcare worker administers the correct medical products to a patient at the patient's bedside will now be described.

In step 810, the bedside terminal 150 identifies the patient to be administered the medical product. This may be done manually by having the healthcare worker enter patient identification information, e.g., patient ID, into the bedside terminal 150 using a keypad. The patient bedside or a wristband worn by the patient. Alternatively, the patient identifier may be provided in a patient RFID tag read by the RF reader 155 of the bedside terminal 150. The patient RFID tag may be attached to a chart or a wristband worn by the patient. In still another alternative, the patient identifier may be preloaded into the memory of the bedside terminal 150.

In step 820, the healthcare worker takes out the medical products he or she intends to administer to the patient. In step 830, the healthcare worker may read the RFID tags 20 of these medical products into the bedside terminal 150 using the RF reader 155. This may be done, e.g., by placing the medical products in close proximity to the RF reader 155. Alternatively, the RF reader 155 may be located at an entrance, e.g., a doorway, of the patient's room for automatically reading the RFID tags 20 of these medical products as the healthcare worker enters the patient's room carrying these medical products.

In step 840, the bedside terminal 150 verifies that the patient present is the correct patient to receive the medical products proposed by the healthcare worker. The bedside terminal 150 may do this by comparing the medical product information read from the RFID tags 20 with information of the medical products to be administered to the patient, which may be downloaded to the bedside terminal 155 from the associated patient file in the database 120. The comparison may include comparing dosage information read from the RFID 20 tags with dosage information from the associated patient file to confirm that the patient is receiving the correct dosage. Alternatively, or in addition, the bedside terminal 150 may compare intended patient information, e.g., patient ID, read from the RFID tags 20 with the patient identifier in the bedside terminal 150. The bedside terminal 150 may also check for any adverse drug interaction between the medical products brought for the patient and medical products administered to the patient earlier by consulting a drug interaction database. The bedside terminal 150 may determine that the medical products should not be administered to the patient if it detects a mismatch in any one of these comparisons and/or an adverse drug interaction. Alternatively, the management computer 115 may perform the verification step by having the bedside terminal 150 transmit the information read from the RFID tags 20 to the management computer 115.

In step 850, the bedside terminal 150 indicates to the healthcare worker whether to proceed with administration of the medical products based on the above verification, e.g., by transmitting a "go/no go" signal to the healthcare worker. The "go/no go" signal may be transmitted to the healthcare worker using a variety of output devices, including LCD displays, LEDs, and the like. For example, the "go" signal may be a green light emitted from a light indicator and the "no go" signal may be a red light emitted from a light indicator. In addition, the "no go" signal may be a buzzing sound emitted from a buzzer.

When the bedside terminal 150 indicates to the healthcare worker not to proceed with administration, the bedside terminal 150 may provide the healthcare with the specifics of any detected mismatch via a display 730, such as the identity of a medical product not to be administered to the patient. The bedside terminal 150 may then give the healthcare worker an opportunity to correct the mismatch by repeating steps 820–850. In addition, the bedside terminal 150 may transmit information of the mismatch to the management computer 115 so that the management computer 115 may include a report of the mismatch in the associated healthcare worker file and/or patient file. The report may include specific information of the mismatch, including incorrect medical products, incorrect dosage, and the like. The administrators of the healthcare facility may use the report to evaluate the work performance of the healthcare worker, including looking for any patterns in medication errors made by the healthcare worker. The administrators may also pool together and evaluate the reports from different healthcare worker files to look for any system-wide pattern in medication errors at the healthcare facility. Optionally, the healthcare worker may take the improper or unused medical product(s) to a return bin, e.g., in the original dispensing unit, to a different dispensing unit, or in a separate return medication station, as explained further below.

When the bedside terminal 150 indicates to the healthcare worker to proceed with administration, the bedside terminal 150 may record information related to the administration of the medical products to the patient. This information may include the product names and dosages of the medical products administered to the patient, the date and time of administration and/or the identity of the healthcare worker administering the medical products. The bedside terminal 150 may transmit the recorded administration information to the management computer 115 to be included in the associated patient file in the database 120. In addition, the management computer 115 may automatically enter the administration information into an electronic medication administration record (MAR) associated with the patient, which may be stored in the database 120. This has the advantage of not relying on the healthcare worker administering the medical products to the patient to record manually the administration of the medical products in a MAR, which may be prone to human error. In addition, this has the advantage of providing up-to-the-minute updates to the MAR and standardizing the documentation in the MAR. The management computer 115 may also enter the administration information into the billing record of the patient in order to bill the patient's insurer for the medical products administered to the patient. This may help ensure that the patient's insurer is timely billed for only those medical products actually administered to the patient.

In one embodiment, the bedside terminal 150 may include an input device 720, e.g., a keypad or touch screen, to enable a healthcare worker to enter observations of the patient into the bedside terminal, such as the condition of the patient at time of administration of the medical products and the like. The bedside terminal 150 may then transmit these observations to the management computer 115 to be included in the patient file and/or MAR associated with the patient.

In another embodiment, after the healthcare worker has completed a round, the healthcare worker may indicate to the management computer 115 that he or she has completed the round, e.g., via a checkout terminal (not shown) linked to the management computer 115. The management computer 115 may then verify that the healthcare worker has administered all of the medical products to the patients assigned to him or her in that round. The management computer 115 may do this by comparing the medical products that the healthcare worker removed from the dispensing unit with the medical products administered to the patients assigned to him or her in the round. If the management computer detects a mismatch, then the management computer 115 may immediately notify the healthcare worker of the detected mismatch via a terminal linked to the management computer 115. This may occur, for example, if the healthcare worker becomes distracted by an emergency during the round and forgets to administer medical products to one or more of his or her patients. The notification may include specific information of the mismatch, such as the identity of any medical products that were removed from the dispensing unit but not administered to the intended patient.

In many cases, it is critical that medical products are administered to a patient within a period of time after they are removed from the dispensing unit 410. For example, certain medical products, e.g., chemotherapy drugs, quickly loss their potency when placed in an aqueous solution. To address this, the management computer 115 according to an embodiment may monitor the time period between the time that a medical product is removed from the dispensing unit 410 and the time that the medical product is administered to a patient. In this embodiment, when a medical product is removed from the dispensing unit, the dispensing terminal 140 may record the time that the medical product is removed from the dispensing unit 410 and transmit the recorded time to the management computer 115. When the healthcare worker, e.g., nurse, is ready to administer the medical product to the intended patient at the patient's bedside, the bedside terminal 150 may consult with the management computer 115 whether to proceed with the administration. This may be done, e.g., by having the bedside terminal 150 transmit medical product information read from the RFID tags 20 to the management computer 115. The management computer 115 may then retrieve the recorded time that the medical products were removed from the dispensing unit 410 using the received medical product information. The management computer 115 may then compute the time difference between the time of administration and the time that the medical product were removed from the dispensing unit 150. If the time difference exceeds a predetermined time limit for administering the medical product to the patient, then the management computer 115 may notify the bedside terminal 150 not to proceed with the administration of the medical product. The predetermined time limit may be based on a limited stability of the potency of the medical product.

When the time limit for administering a medical product is exceeded, the healthcare worker may contact a physician or pharmacist, e.g., via a phone, to make a judgement call on whether to administer the medical product to the patient. In this embodiment, the physician or pharmacist may view the time difference between administration and removal of the medical products from the dispensing unit 410 on a terminal, e.g., a personal computer, linked to the management computer 115. If the physician or pharmacist determines that it is acceptable to administer the medical product, then he or she may transmit an override command to the management computer 115 to allow the healthcare worker to proceed with administering the medical product to the patient.

If a decision is made not to deliver a medical product to a patient, the unused medical product may be taken to a return bin of a dispensing unit, e.g., the unit from which it was originally removed, another unit, or a special medication station for returned medical products. The RFID tags of the medical products in the return bin (or in the entire dispensing unit) may be read before and after the medical product (or products) is (are) placed in the return bin. A difference between the readings of the RFID tags taken before and after the medical product is returned to the dispensing unit may be used to identify the medical product returned to the dispensing unit. In addition, the processor of the dispensing unit may identify a patient intended to receive the returned medical product, and a notice may be sent, e.g., to the pharmacy, the patient's doctor, a facility administrator, and the like, that the intended patient did not receive the returned medical product. Thus, if the failure to deliver the medical product was mistaken, action may be taken to correct the mistake. If the medical product was not delivered, and it is confirmed that delivery should not be resumed, any administrative action that had been taken assuming that the medical product was being delivered may be adjusted. Thus, the patient's record, billing, and the like may be corrected to accurately indicate the medical products that were actually delivered to the patient.

In addition or alternatively, the processor may transfer an inventory of returned medical products via a communications link to a central database, e.g., maintained by the facility's management computer. For example, if a particular medical product is missing, all of the return bins in the facility may be inventoried or searched to determine whether the medical product has been returned to a return bin in one of the dispensing units. Thus, the location and status of virtually all of the medical products in the facility may be tracked.

Therefore, the invention provides a closed-loop system for tracking and monitoring medical products within a healthcare facility, from the time that the medical products are received by the pharmacy to the time that they are administered to patients. The system of the invention provides up-to-the-minute inventories of the medical products in the pharmacy and medication-dispensing units of the healthcare facility. In addition, the system tracks the delivery of medical products from the pharmacy to the medication-dispensing units placed throughout the healthcare facility by verifying that the dispensing units receive medical products withdrawn from the pharmacy. Furthermore, the system monitors the removal of medical products from the dispensing units by verifying that healthcare workers only remove those medical products to be administered to patients assigned to the healthcare workers. The system also tracks the delivery of medical products from the dispensing unit to patients by verifying that healthcare workers administer all of the medical products removed from the dispensing unit to the intended patients. The system also monitors the administration of the medical products to patients by verifying that the patients receive the correct medical products before administration, thereby reducing the risk of adverse drug events. In addition, the system reduces the risk of lost or stolen medical products by immediately notifying healthcare workers and/or administrators of any missing medical products so that they may take appropriate action to recover and/or investigate the missing medical products.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for monitoring unit dose medical products stored in a medication-dispensing unit, each of the unit dose medical products comprising a Radio Frequency Identification (RFID) tag uniquely associated therewith, the method comprising:

removing a unit dose medical product from the dispensing unit;

identifying the unit dose medical product removed from the dispensing unit by detecting removal of the RFID tag associated with the medical product removed from the dispensing unit;

verifying that the unit dose medical product removed from the dispensing unit is authorized to be removed from the dispensing unit, the verifying step comprising comparing a product name identified by the RFID tag removed from the dispensing unit with a product authorized to be removed from the dispensing unit; and further comprising identifying a patient, and wherein the verifying step further comprises comparing a product name identified by the RFID tag removed from the dispensing unit with a list of medical products scheduled for delivery to the identified patient and assigning the removed unit dose medical product to an individual patent to ensure that the correct medical product is delivered to the patient.

2. The method of claim 1, further comprising:

returning a medical product to the dispensing unit; and reading an RFID tag associated with the medical product to identify the returned medical product.

3. The method of claim 2, further comprising determining an intended patient for the returned medical product, and sending a notice that the intended patient did not receive the returned medical product.

4. A method for monitoring unit dose medical products as in claim 1 wherein the unit dose medical products are medication containers each comprising one of a vial, bottle or bag.

5. A method for monitoring unit dose medical products stored in a medication-dispensing unit, each of the unit dose medical products comprising a Radio Frequency Identification (RFID) tag uniquely associated therewith, the method comprising:

removing a unit dose medical product from the dispensing unit;

identifying the unit dose medical product removed from the dispensing unit by detecting removal of the RFID tag associated with the medical product removed from the dispensing unit, wherein the steps of identifying the medical product removed from the dispensing unit further comprises:

reading the RFID tags of the medical products in the dispensing unit before the medical product is removed from the dispensing unit;

reading the RFID tags of the medical products in the dispensing unit after the medical product is removed from the dispensing unit and assigning the unit dose medical products to respective individual patients to ensure that correct medical products are delivered to the patients; and determining a difference between the readings of the RFID tags taken before and after the medical product is removed from the dispensing unit to identify the unit dose medical product removed.

6. The method of claim 5, wherein the verifying step comprises comparing a product name identified by the RFID tag removed from the dispensing unit with a product name authorized to be removed from the dispensing unit.

7. The method of claim 6, wherein the product name of the medical product removed from the dispensing unit is obtained by reading the RFID tags before the medical product is removed from the dispensing unit.

8. The method of claim 5, further comprising identifying a patient, and wherein the verifying step further comprises comparing a product name identified by the RFID tag removed from the dispensing unit with a list products scheduled for delivery to the identified patient.

9. The method of claim 8, wherein the product name of the medical product removed from the dispensing unit is obtained by reading the REID tags before the medical product is removed from the dispensing unit.

10. A method for monitoring unit dose medical products as in claim 5 wherein the unit dose medical product removed from the dispensing unit is assigned to an individual patient upon removal from the dispensing unit.

11. A method for monitoring removal of unit dose medical products stored in a medication-dispensing unit, each of the unit dose medical products comprising a Radio Frequency Identification (RFID) tag uniquely associated therewith, the method comprising:

reading the RFID tags of the unit dose medical products in the dispensing unit before removing one or more medical products from the dispensing unit;

removing one or more unit dose medical products from the dispensing unit;

reading the RFID tags of the medical products in the dispensing unit after the one or more medical products are removed from the dispensing unit; and determining a difference between the readings of the RFID tags taken before and after the one or more medical products are removed from the dispensing unit to identify the one or more unit dose medical products removed from the dispensing unit, and assigning the unit dose medical products to respective individual patients to ensure that correct medical products are delivered to the patients.

12. The method of claim 11, further comprising verifying that the one or more medical products removed from the dispensing unit are authorized to be removed from the dispensing unit.

13. The method of claim 12, wherein the verifying step comprises comparing a product name identified by an RFID tag removed from the dispensing unit with a product name authorized to be removed from the dispensing unit.

14. The method of claim 12, further comprising identifying a patient, and wherein the verifying step further comprises comparing a product name identified by the RFID tag removed from the dispensing unit with a list of medical products scheduled for delivery to the identified patient.

15. The method of claim 11, further comprising transmitting an inventory notice from the dispensing unit when a quantity of RFID tags stored within the dispensing unit falls below a threshold.

16. The method of claim 11, further comprising:

returning a medical product to the dispensing unit;

reading the RFID tags of the medical products in the dispensing unit after the medical product is returned to the dispensing unit; and determining a difference between the readings of the RFID tags taken before and after the medical products are returned to the dispensing unit to identify the medical product returned to the dispensing unit.

17. The method of claim 16, further comprising determining an intended patient for the returned medical product, and sending a notice that the intended patient did not receive the returned medical product.

18. An apparatus for tracking unit dose medical products, each of the unit dose medical products having a radio frequency identification (RFID) tag uniquely associated therewith, the apparatus comprising a casing comprising a plurality of lockable drawers for receiving one or more unit dose medical products therein, a reader for reading the RFID tags associated with the unit dose medical products in the drawers, a processor coupled to the reader for receiving and processing readings of the RFID tags in the drawer to identify medical products in the drawer, wherein the processor can verify that a unit dose medical product removed from a drawer is authorized to be removed and the removed medical product is assigned to an individual patient as the medical product is removed, and wherein the processor can identify a medical product removed from a drawer by determining a difference between readings of RFID tags in the drawer taken before and after a medical product is removed.

19. The apparatus of claim 18, wherein the product identifier comprises at least one of a product name, a serial number, a product lot number, and a patient identifier.

20. The apparatus of claim 18, further comprising a display coupled to the processor, and wherein the processor displays a mismatch notification on the display when the processor detects a mismatch between the product identifier read from the RFID tag of the removed medical product and the product identifier of the medical product authorized to be removed.

21. The apparatus of claim 20, wherein the mismatch notification comprises the product identifier read from the RFID tag of the removed medical product and the product identifier of the medical product authorized to be removed.

22. The apparatus of claims 18, wherein the apparatus includes a single reader for reading the RFID tags of all medical products in the casing.

23. The apparatus of claim 18, wherein each drawer comprises a plurality of compartments, and wherein the reader comprises a plurality of readers for reading the RFID tags of medical products in respective compartments.

24. The apparatus of claim 18, further comprising an input device coupled to the processor for identifying a patient to be associated with one or more medical products being removed from the drawer.

25. The apparatus of claim 18, further comprising a return drawer for returning unused medical products, and a reader for reading an RFID tag of any returned medical product placed in the return drawer, the processor coupled to the reader for identifying the returned medical product.

26. A method for monitoring removal of unit does medical products stored in a medication-dispensing unit, each of the unit dose medical products comprising a Radio Frequency Identification (RFID) tag uniquely associated therewith, the method comprising:

reading the RFID tags of the unit dose medical products in the dispensing unit before removing one or more medical products from the dispensing unit;

removing one or more unit dose medical products from the dispensing unit;

reading the RFID tags of the medical products in the dispensing unit after the one or more medical products are removed from the dispensing unit;

determining a difference between the readings of the RFID tags taken before and after the one or more medical products are moved from the dispensing unit to identify the one or more unit dose medical products removed from the dispensing unit, returning a unit dose medical product to the dispensing unit;

reading the RFID tags of the medical products in the dispensing unit after the medical product is returned to the dispensing unit; and determining a difference between the readings of the RFID tags taken before and after the medical products are returned to the dispensing unit to identify the medical product returned to the dispensing unit.

27. The method of claim 26 further comprising determining an intended patient for the returned medical product, and sending a notice that the intended patient did not receive the returned medical product.

28. The method of claim 26 wherein a returned medical product cannot be removed from the dispensing unit without gaining authorization to override a lock and open the unit for removal.

* * * * *